United States Patent
Murray et al.

(10) Patent No.: US 6,753,345 B2
(45) Date of Patent: *Jun. 22, 2004

(54) 7-HEXANOLYTAXOL AND METHODS FOR PREPARING THE SAME

(75) Inventors: Christopher K. Murray, Longmont, CO (US); Qun Y. Zheng, Wayne, NJ (US); Sagar R. Shakya, Brantford (CA)

(73) Assignee: Hauser, Inc., El Segundo, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/199,826

(22) Filed: Jul. 19, 2002

(65) Prior Publication Data

US 2003/0083367 A1 May 1, 2003

Related U.S. Application Data

(63) Continuation of application No. 09/688,753, filed on Oct. 16, 2000, now Pat. No. 6,469,050, which is a continuation of application No. 09/058,036, filed on Apr. 10, 1998, now Pat. No. 6,136,988.

(51) Int. Cl.$^7$ ............... A61K 31/337; C07D 305/14
(52) U.S. Cl. ............... 514/449; 549/510; 549/511
(58) Field of Search ............... 514/449; 549/510, 549/511

(56) References Cited

U.S. PATENT DOCUMENTS

| | | | |
|---|---|---|---|
| 5,227,400 A | 7/1993 | Holton et al. | 514/400 |
| 5,243,045 A | 9/1993 | Holton et al. | 514/60 |
| 5,250,683 A | 10/1993 | Holton et al. | 544/60 |
| 5,283,253 A | 2/1994 | Holton et al. | 514/444 |
| 5,284,864 A | 2/1994 | Holton et al. | 514/444 |
| 5,352,806 A | 10/1994 | Gunawardana et al. | 549/510 |
| 5,380,751 A | 1/1995 | Chen et al. | 514/449 |
| 5,422,364 A | 6/1995 | Nicolaou et al. | 514/449 |
| 5,580,899 A | 12/1996 | Mayhew et al. | 514/449 |
| 5,721,268 A | 2/1998 | Holton et al. | 514/449 |
| 5,939,567 A | 8/1999 | Mayhew et al. | 549/510 |
| 6,469,050 B1 * | 10/2002 | Murray et al. | 514/449 |

FOREIGN PATENT DOCUMENTS

WO    WO 96/21658    7/1996

OTHER PUBLICATIONS

Georg, et al., "7–O–Acylpaclitaxel Analogues", Bioorganic & Medicinal Chemistry Letters, vol. 7, No. 14, 1997, pp. 1829–1832.

Iwao Ojima et al., "Structure–Activity Relationship Studies of New Taxanes as Reversal Agents for Multi–Drug Resistance in Cancer Cells," MEDI, Apr. 2, 1998.

Zheng, et al., "Deacetylation of Paclitaxel and other Taxanes" Tetrahedron letters. NI, Elsevier Science Publishers, Amsterdam, vol. 36, No. 12, Mar., 20, 1995, pp. 2001–2004.

* cited by examiner

Primary Examiner—Ba K. Trinh
(74) Attorney, Agent, or Firm—Jones Day (57) ABSTRACT

An antitumor compound of formula (5):

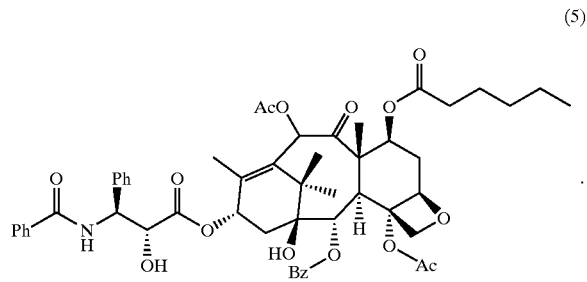

(5)

Also provided by the present invention is a method of preparing a compound of formula (5) whereby diesterification of the alcohol groups located at the 2' and 7 positions of paclitaxel is followed by the hydrolysis of the 2' hexanoate group resulting in 7-hexanoyltaxol.

19 Claims, 11 Drawing Sheets

7-HEXANOLYTAXOL AND METHODS FOR PREPARING THE SAME

RELATED DOCUMENTS

The present application is a continuation of U.S. patent application Ser. No. 09/688,753, filed Oct. 16, 2000, now U.S. Pat. No. 6,469,050 B1, which is a Continuation Application of U.S. patent application Ser. No. 09/058,036, filed April 10, 1998, entitled "7-Hexanoyltaxol and Method for Preparing the Same", now U.S. Pat. No. 6,136,988, which patent application references Disclosure Document entitled "Preparation of 7-Hexanoyltaxol: A Novel Paclitaxel Derivative," No.: 396746, filed Apr. 10, 1996.

BACKGROUND OF THE INVENTION

1. Field of the Invention

The present invention relates to a paclitaxel derivative which exhibits an antitumor activity greater than that of paclitaxel.

2. Description of the State of Art

Between the years 1958 and 1980, extracts of over 35,000 plant species were tested for anticancer activity as part of an NCL-sponsored program. Chemists Monroe E. Wall and M. C. Wani first isolated a crude extract concentrate from yew tree (*Taxus brevifolia*) bark and wood samples in 1963. Initial screening showed the extract to be a potential anticancer agent, being very active against an unusually wide range of rodent cancers. Isolation of the active agent in the crude extract took several years due to the very low concentrations of the agent present in the plants. The active agent was identified, the structure determined and the compound, in 1971, was named taxol, which is now generically referred to as paclitaxel (1):

(1)

The naturally occurring diterpenoid, paclitaxel (1), is one of the most exciting discoveries in the field of cancer chemotherapy. In 1979, Susan B. Horwitz and co-workers established that, while paclitaxel was an antimiotic inhibitor, the mechanism was unique in that it stabilizes microtubules and inhibits depolymerization back to tubulin; this was quite the opposite effect of other antimiotic agents which all bind to soluble tubulin and inhibit the polymerization of tubulin to form microtubules. See, *Nature,* 227:655–667 (1979). Thus, taxol increases the time required for cell division which in turn inhibits tumor activity.

Since the discovery of paclitaxel, over one hundred compounds having the taxane skeleton have been isolated from various Taxus species, listed below are but a few of the representative structures of the more notable taxol analogues.

(2)

| | | | |
|---|---|---|---|
| (b) Paclitaxel (taxol A) | $R_1$ = H | $R_2$ = Ac | $R_3$ = $C_6H_5$ |
| (c) Cephalomannine (taxol B) | $R_1$ = H | $R_2$ = Ac | $R_3$ = $CH_3CH{=}C(CH_3)$ |
| (d) Taxol C | $R_1$ = H | $R_2$ = Ac | $R_3$ = n-$C_5H_{11}$ |
| (e) 10-deacetyltaxol A | $R_1$ = $R_2$ = H | | $R_3$ = $C_6H_5$ |
| (f) 10-deacetyltaxol B | $R_1$ = $R_2$ = H | | $R_3$ = $CH_3CH{=}C(CH_3)$ |
| (g) 10-deacetyltaxol C | $R_1$ = $R_2$ = H | | $R_3$ = n-$C_5H_{11}$ |

Despite paclitaxel's excellent activity in model tumor systems, research progressed at a rather a slow pace and its development was fraught with many obstacles including scarcity of the drug (owing to low abundance of Yew tissue), extremely low aqueous solubility, and toxicities. Problems in drug supply have largely been alleviated, not only as a result of more efficient collection and extraction of plant material, but also because of the progress made in the complete and semi-synthesis of the compound paclitaxel. Three total synthesis have been carried out to date. The Holden group and Nicolaou group published their approaches in 1994, and more recently, Danishefsky and co-workers reported their route to paclitaxel. See, *J. Am. Chem. Soc.,* 116:1597–1599 (1994); *Nature,* 367:630 (1994), *J. Chem. Soc. Chem. Commun.,* 295 (1994), and *J. Am. Chem. Soc.,* 116:1591 (1994); and *J. Am. Chem. Soc.,* 118:2843 (1996), respectively, and which are hereby incorporated by reference. The extremely low aqueous solubility and toxicity obstacles, however, remain more difficult to overcome.

Paclitaxel is a complex diterpenoid which comprises a bulky, fused ring system and an extended side chain at the C-13 position that is required for activity. This complex structure further contains 11 chiral centres with 2048 possible diastcreoisomeric forms. Relatively hydrophilic domains exist in the molecule around the vicinity of the C-7 through C-10 and C-1' through C-2' positions. However, hydrophobic domains of the taxane backbone and side chain contribute to the overall poor aqueous solubility of the compound. In order to administer human doses in a reasonable volume, paclitaxel is currently formulated for clinical use in a mixture of anhydrous ethanol and polyethoxylated castor oil (Cremophor EL®), a clear, oily, viscous, yellow surfactant. In addition to the potential problems of physical instability, the most significant problem with the current clinical paclitaxel formulation is that the Cremophor EL® vehicle possesses pharmacological activity. While a variety of drugs are administered in Cremophor EL®, the dose of Cremophor EL® that accompanies a dose of paclitaxel is the highest for any marketed drug. Cremophor EL® has been observed to cause serious or fatal hypersensitivity episodes, and vehicle toxicity may be largely responsible for fatal or life-threatening anaphylactic reactions observed upon rapid infusion of paclitaxel into animals or humans.

In light of the serious risks associated with the current intravenous formulations of paclitaxel, efforts to develop safe, convenient, and efficacious paclitaxel formulations are ongoing. However, the majority of approaches underway to solve the problems associated with paclitaxel are the synthesis and evaluation of a second generation of paclitaxel analogues.

10-deacetylbaccatin III (2) and baccatin III (3)

(2) 10-deacetyl baccatin III, R=H
(3) baccatin III, R=Ac are diterpenes that are more readily available than paclitaxel and are known synthetic precursors of paclitaxel and its analogues. Their structural complexity is less than that of paclitaxel's and therefore, 10-deacetylbaccatin III (2) and baccatin III (3) are also valuable starting materials for structural modifications at the diterpene part of the paclitaxel molecule.

10-deacetylbaccatin III was used as the starting material for the semisynthetic compound docetaxel (4) commonly referred to as Taxotère®, developed by French researchers from the Institut de Chèmie de Substances Naturelles and Rhône-Poulenc Rorer in 1981.

The lateral side chain located at C-13 position, which is responsible for its cytotoxic effect, is added chemically. Docetaxel differs structurally from paclitaxel at the C-10 position on the baccatin ring and at the C-3' position on the lateral side chain. See, "Biologically Active Taxol Analogues with Deleted A-Ring Side Chain Substituents and Variable C-2' Configuration," *J. Med. Chem.*, 34:1176–1184 (1991); "Relationships between the Structure of Taxol Analogues and Their Antimitotic Activity," *J. Med. Chem.*, 34:992–998 (1991). Docetaxel is twice as potent an inhibitor of microtubule depolymerization as paclitaxel. The in vitro cytotoxicity of docetaxel in murine and human tumor cell lines and its in vivo preclinical activity in murine and human xenografts have been impressive. Docetaxel has displayed higher cytotoxic activity than other antineoplastic agents such as paclitaxel, cisplatin, cyclophosphamide, and doxorubicin against the same tumor models. While docetaxel is a promising antitumor agent with a broad spectrum it, like paclitaxel, suffers low aqueous solubility. The fact remains however, that a potent analogue of paclitaxel having promising activity was developed by making a simple side chain modifications at the 3' amide. Encouraged by this exciting result other researchers began modifications to each position of the diterpene core hoping to develop a structural analogue of paclitaxel which overcomes the problems associated with paclitaxel; however, to date, none have been developed.

There is still a need, therefore, for developing structural analogues of paclitaxel which have less formulation problems and equivalent or greater potency than that of paclitaxel.

SUMMARY OF THE INVENTION

Accordingly, it is an object of this invention to provide a structural analogue of paclitaxel which demonstrates antitumor activity and a method for the preparation of the same. More specifically the present invention provides a paclitaxel derivative of formula (5)

having antitumor activity.

Another object of the present invention is to provide a method for the preparation of 7-hexanoyltaxol.

Additional objects, advantages and novel features of this invention shall be set forth in part in the description and examples that follow, and in part will become apparent to those skilled in the art upon examination of the following specification or may be learned by the practice of the invention. The objects and advantages of the invention may be realized and attained by means of the instrumentalities, combinations, compositions, and methods particularly pointed out in the appended claims.

To achieve the foregoing and other objects and in accordance with the purposes of the present invention, as embodied and broadly described therein the method, and compositions produced thereby, of this invention comprises converting the alcohols located at the 2' and 7 positions of paclitaxel to esters, resulting in an intermediate composition. Selective hydrolysis of the 2'-ester leads to the desired product.

BRIEF DESCRIPTION OF THE DRAWINGS

The accompanying drawings, which are incorporated in and form a part of the specification, illustrate the preferred embodiments of the present invention, and together with the description serve to explain the principles of the invention.

In all of the drawings which follow, the horizontal axis depicts various dilutions of the test compound, ranging from $10^{-4}$ to $10^{-14}$ molar, that were exposed to a specified cancer. The vertical axis (percentage growth) depicts the growth of the specified cancer cell line when exposed to a specific concentration of the tested compound as compared to the growth of the same cancer cell line not exposed to any compound.

DETAILED DESCRIPTION OF THE PREFERRED EMBODIMENT

The present invention provides a novel taxol derivative of formula (7)

(7)

wherein R may be a monovalent organic compound, a monovalent aliphatic compound such as a hydrocarbon or a hetero-acyclic group, or a monovalent cyclic group such as an alicyclic or aromatic group wherein the monovalent alicyclic group comprises monovalent carbocyclic and heterocyclic groups and the monovalent aromatic group comprises monovalent carboaromatic groups and monovalent hetero-aromatic groups. More specifically R may be a branched or unbranched alkyl, alkenyl, alkynyl group or an aryl group, the synthesis of which can be accomplished by a wide variety of methods.

Figure 1:
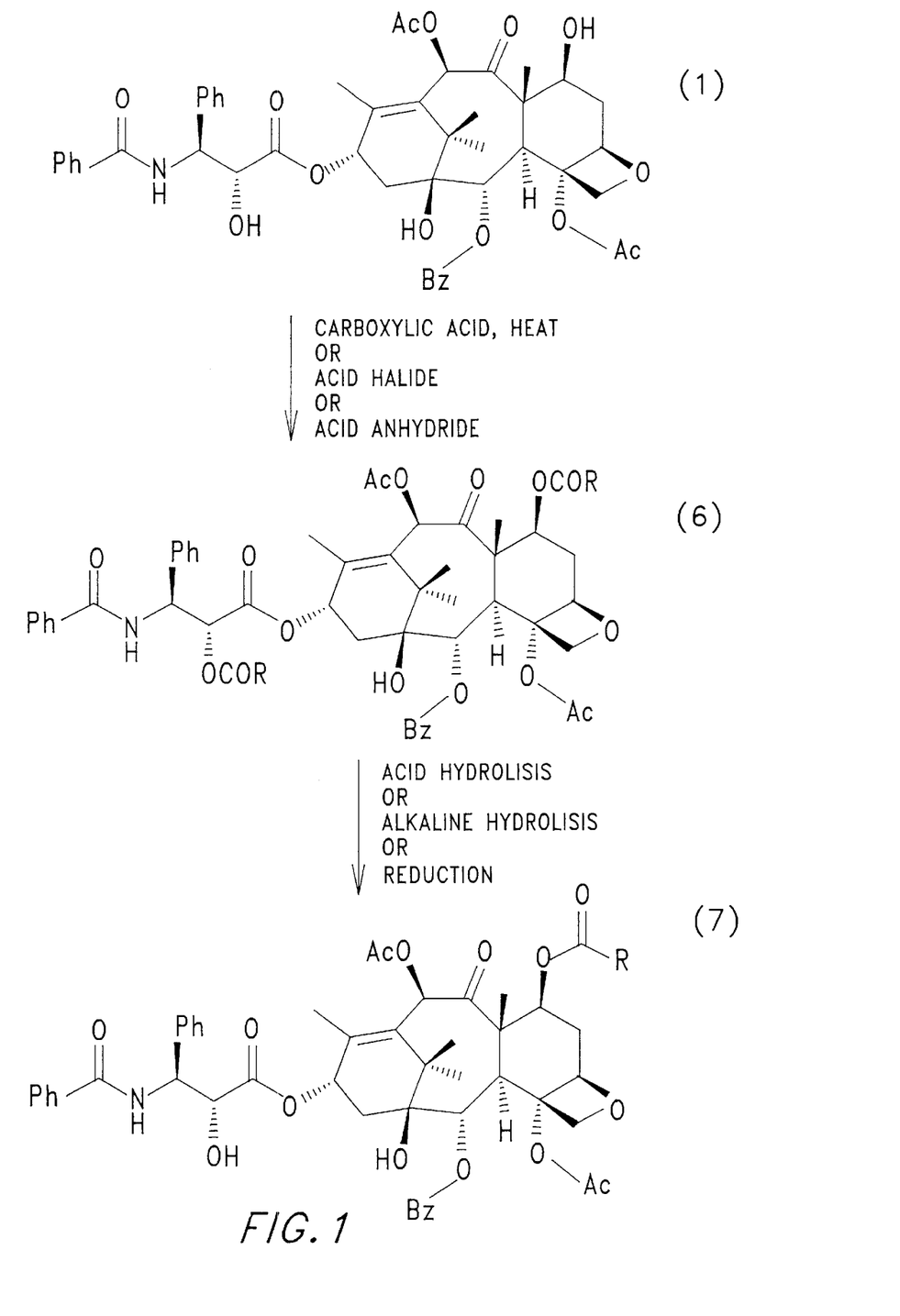
FIG. 1 depicts a schematic illustrating the various synthetic routes used in the preparation of the compositions of the present invention.

As shown in FIG. 1, the alcohols located at the 2' and 7 positions of the paclitaxel compound (1) may be converted to esters prepared by adding a reagent, such as a carboxylic acid, an acid halide or an acid anhydride, having the desired R group, to a solution of paclitaxel. The necessary reaction conditions for preparing esters from alcohols are well known and understood in the art. The resulting intermediate (6) is subsequently purified and the ester located at the 2' position is either hydrolyzed or reduced resulting in product (7).

Figure 1A:
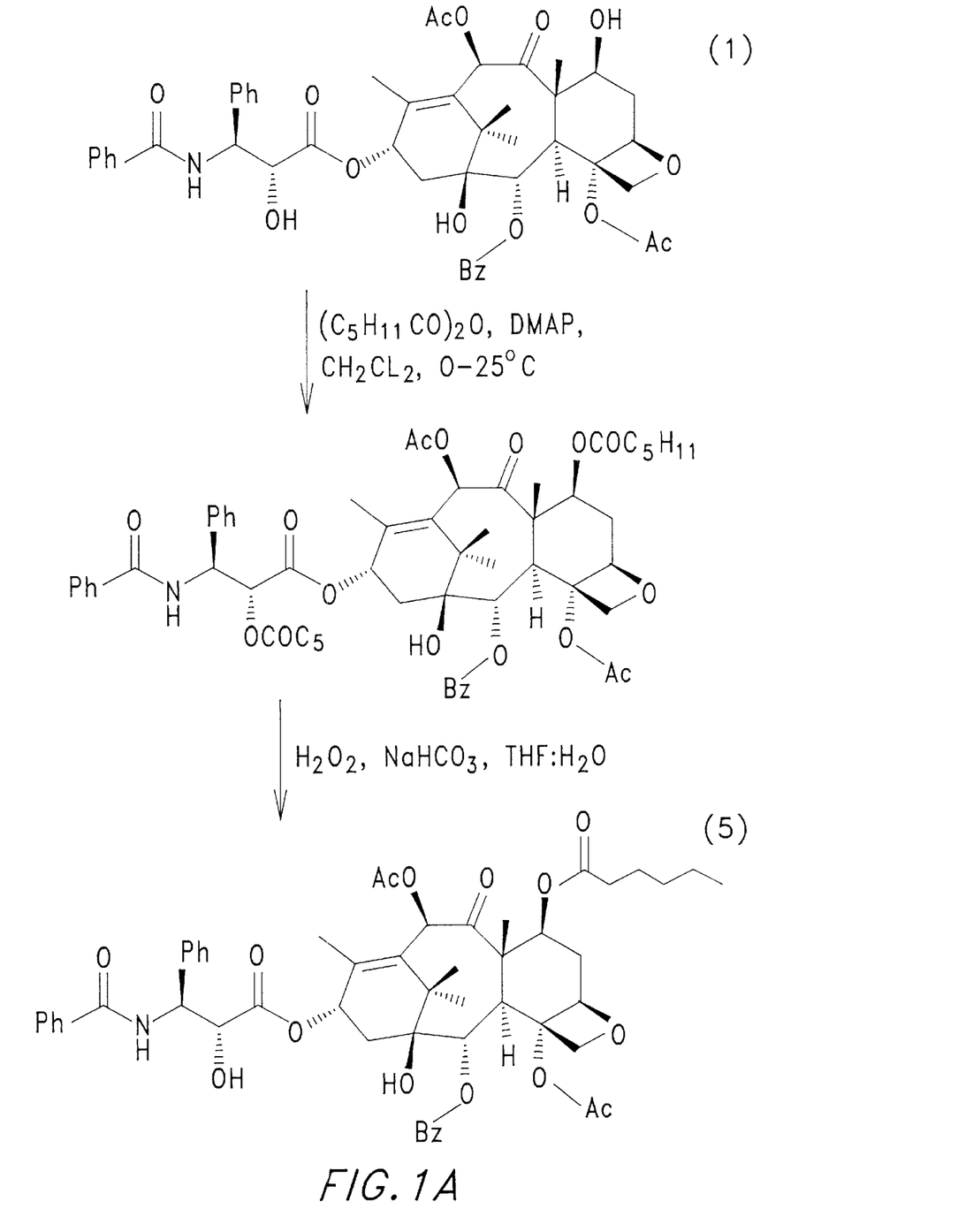
FIG. 1a depicts a schematic illustrating the preferred method of preparing the preferred composition of the present invention

In the preferred embodiment, shown in FIG. 1a, a compound of formula (5), is produced by mixing an acid anhydride, such as hexanoic acid, to a mixture of paclitaxel (1). The diesterification of the alcohols located at the 2' and 7 positions of paclitaxel result in an intermediate bis 2',7-hexanoyltaxol compound. The selective removal of the 2'-hexanoate group by hydrolysis results in the desired 7-hexanoyltaxol compound (5).

To determine the cytotoxicity of 7-hexanoyltaxol as compared to taxol, screening assays were performed; these activities are summarized in Table I (set out below). The screening assay is performed on 96-well microtitre plates. Relatively high initial inoculation densities are used, in order to permit measurement of "time-zero" values and to enhance the screen's ability to detect and provide some differentiation between antiproliferative and cytotoxic response parameters. The specific inoculation densities (which range from 5,000 to 40,000 cells/well) used for each cell line are those which, for the respective line, were determined to give an optical density signal for both the "time-zero" value (at 24 hours) and the "no-drug" control (at 72 hours) above the noise level and within the linear range of the end-point assay (which measures cellular protein). The inoculated microtitre plates are pre-incubated for 24 hours at 37° C. prior to drug additions. The five drug dilutions tested routinely range from $10^{-4}$ to $10^{-8}$ molar. Higher or lower concentration ranges may be selected on a nonroutine basis if appropriate solubility and/or prior biological information or other screening data so dictate. Duplicate wells are prepared for all concentrations; "time-zero" and "no drug" controls are also provided for each test. The minimum amount of compound required for a 1-time evaluation in the routine screen can be calculated from the knowledge that each test requires a total of approximately 40 ml (0.04 liter) of cell culture medium containing the highest desired drug concentration. Thus, the amount (grams) of sample required (assuming an upper test concentration limit of $10^{-4}$ M) is: molecular weight of compound$\times 10^{-4} \times 0.04$. After a 48 hour incubation (37° C. with the test compound, the cells are fixed in situ to the bottoms of the microtitre wells by addition of 50 µl of either 50% trichloroacetic acid (for adherent cell lines) or 80% trichloroacetic acid (for settled cell suspension lines), followed by incubation for 60 minutes at 4° C. The cellular protein in each well is assayed using a sulfarhodamine B (SRB) stain procedure. Briefly, after discarding the supernatants, the microtitre plates are washed 5 times with deionized water and air-dried. One hundred microliters of SRB solution (0.4% w/v in 1% acetic acid) is added to each microtitre well and incubated for 10 minutes at room temperature. Unbound SRB is removed by washing 5 times with 1% acetic acid. The plates are air-dried, the bound stain is solubilized with Tris buffer, and the optical densities read at 515 nm. SRB is a bright pink anionic dye which, in dilute acetic acid, binds electrostatically to the basic amino acids of TCA-fixed cells. Cryopreserved master stocks of all the lines are maintained, and cultures used for screening are replaced from the master stock after no more than twenty passages in the screening laboratory. The cell line panel consists of 60 lines, organized into nine, disease-related subpanels including leukemia, non-small-cell lung cancer, colon, CNS, melanoma, ovarian, renal, prostate and breast cancers.

The response parameters $GI_{50}$ and $LC_{50}$ are interpolated values representing the concentrations at which the percentage growth (PG) is +50 and −50 respectively:

$GI_{50}$ is the concentration for which the PG=+50. At this value the increase from time $t_{zero}$ in the number or mass of cells in the test well is only 50% as much as the corresponding increase in the control well during this period of the experiment. A drug effect of this intensity is interpreted as primary growth inhibition.

TGI is the concentration for which PG=0. At this value the number or mass of cells in the well at the end of the experiment equals the number or mass of cells in the well at time $t_{zero}$. A drug effect of this intensity is regarded as cytostasis.

$LC_{50}$ is the concentration for which the PG=−50. At this value, the number or mass of cells in the test well at the end of the experiment is half that at time $t_{zero}$. This is interpreted as cytotoxicity.

TABLE I

| | $Log_{10}$ $GI_{50}$ | | $Log_{10}$ TGI | | $Log_{10}$ $LC_{50}$ | |
|---|---|---|---|---|---|---|
| Panel/Cell line | 7-Hexanoyl-taxol | Paclitaxel | 7-Hexanoyl-taxol | Paclitaxel | 7-Hexanoyl-taxol | Paclitaxel |
| Leukemia | | | | | | |
| CCRF-CEM | <−8.00 | −11.61 | <−8.00 | >−4.00 | >−4.00 | >−4.00 |
| HL-60(TB) | <−8.00 | −11.57 | <−8.00 | >−4.53 | >−4.00 | >−4.00 |
| K-562 | <−8.00 | −10.83 | −7.05 | >−4.00 | >−4.00 | >−4.00 |
| MOLT-4 | <−8.00 | −11.07 | −4.69 | >−4.00 | >−4.00 | >−4.00 |
| RPMI-8226 | <−8.00 | <−13.00 | >4.00 | >−4.00 | >−4.00 | >−4.00 |
| SR | <−8.00 | −8.34 | — | >−4.00 | >−4.00 | >−4.00 |
| Non-Small Cell Lung Cancer | | | | | | |
| EKVX | −6.40 | — | −4.29 | — | >−4.00 | >4.00 |
| HOP-62 | −7.85 | −9.67 | −6.52 | −4.80 | −4.05 | −4.05 |
| NCI-H226 | <−8.00 | — | −4.76 | — | >−4.00 | >4.00 |
| NCI-H23 | <−8.00 | — | −4.86 | — | −4.34 | −4.34 |
| NCI-H322M | −7.70 | −10.12 | −4.51 | −4.46 | >−4.00 | >−4.00 |
| NCI-H460 | <−8.00 | −12.16 | −4.75 | −4.92 | >−4.00 | >−4.00 |
| NCI-H522 | <−8.00 | <−13.00 | −5.91 | −11.20 | >−4.00 | >−4.00 |
| Colon Cancer | | | | | | |
| COLO 205 | <−8.00 | −11.07 | −7.38 | — | −4.58 | >−4.58 |
| HCC-2998 | <−8.00 | −12.34 | −7.35 | −4.77 | −5.08 | −5.08 |
| HCT-116 | <−8.00 | <−13.00 | −4.94 | −4.82 | >−4.00 | >−4.00 |
| HT29 | <−8.00 | <−13.00 | −4.95 | — | −4.48 | −4.48 |
| KM12 | <−8.00 | −11.43 | −4.90 | −4.36 | >−4.00 | >−4.00 |
| SW-620 | <−8.00 | −11.60 | >−4.00 | >−4.00 | >−4.00 | >−4.00 |
| CNS Cancer | | | | | | |
| SF-268 | <−8.00 | — | −4.95 | — | >−4.00 | — |
| SF-295 | <−8.00 | — | −6.41 | — | >−4.00 | — |
| SF-539 | <−8.00 | −11.09 | −7.32 | — | −5.82 | >−4.00 |
| SNB-19 | −7.99 | −8.98 | −4.53 | >−4.00 | >−4.00 | >−4.00 |
| SNB-75 | <−8.00 | — | −7.41 | — | >−4.00 | — |
| U251 | <−8.00 | −11.29 | −4.98 | −4.32 | −4.49 | −4.15 |
| Melanoma | | | | | | |
| LOX-IMVI | — | −11.80 | −4.68 | −4.65 | −4.24 | >−4.15 |
| MALME-3M | <−8.00 | — | −4.65 | −4.46 | −4.09 | −4.11 |
| M14 | <−8.00 | −11.73 | −7.94 | −4.62 | −5.80 | −4.13 |
| SK-MEL-2 | −7.03 | −9.53 | −4.56 | — | >−4.00 | >−4.00 |

TABLE I-continued

| | Log$_{10}$ GI$_{50}$ | | Log$_{10}$ TGI | | Log$_{10}$ LC$_{50}$ | |
|---|---|---|---|---|---|---|
| Panel/Cell line | 7-Hexanoyl-taxol | Paclitaxel | 7-Hexanoyl-taxol | Paclitaxel | 7-Hexanoyl-taxol | Paclitaxel |
| SK-MEL-28 | <−8.00 | — | −4.33 | — | >−4.00 | — |
| SK-MEL-5 | <−8.00 | — | −4.56 | — | >−4.00 | — |
| UACC-257 | — | −10.30 | −4.00 | −4.52 | >−4.00 | −4.03 |
| UACC-62 | <−8.00 | −10.46 | −4.78 | −4.71 | >−4.00 | −4.19 |
| Ovarian | | | | | | |
| IGR-OV1 | <−8.00 | −8.61 | −4.52 | −4.19 | >−4.00 | >−4.00 |
| OVCAR-3 | <−8.00 | −10.40 | −7.65 | −4.55 | −4.68 | >−4.00 |
| OVCAR-4 | −5.80 | −5.80 | −4.21 | −4.19 | >−4.00 | >−4.00 |
| OVCAR-5 | <−8.00 | −9.38 | −5.47 | −4.92 | −4.47 | >−4.00 |
| OVCAR-6 | <−8.00 | −10.75 | −4.88 | — | −4.07 | >−4.00 |
| SK-OV-3 | <−8.00 | — | −4.84 | — | −4.04 | — |
| Renal Cancer | | | | | | |
| 786-0 | <−8.00 | −8.01 | −4.88 | >−4.00 | −4.44 | >−4.00 |
| A498 | <−8.00 | −7.14 | −7.29 | — | >−4.00 | −4.13 |
| ACHN | −7.02 | — | >−4.00 | — | >−4.00 | — |
| CAKI-1 | −6.58 | — | −4.52 | — | >−4.00 | — |
| RXF-393 | <−8.00 | −8.32 | <8.00 | −4.90 | −4.04 | −4.45 |
| SN12C | <−8.00 | −9.53 | >−4.00 | −4.04 | >−4.00 | >−4.00 |
| TK-10 | −7.49 | −7.89 | −4.45 | >−4.00 | >−4.00 | >−4.00 |
| UO-31 | −7.19 | −6.09 | >−4.00 | −4.29 | >−4.00 | >−4.00 |
| Prostate Cancer | | | | | | |
| PC-3 | <−8.00 | −10.85 | −5.48 | >−4.00 | >−4.00 | >−4.00 |
| DU-145 | <−8.00 | −9.38 | −7.00 | >−4.00 | −4.43 | >−4.00 |
| Breast Cancer | | | | | | |
| MCF7 | <−8.00 | −11.69 | −4.73 | −4.05 | >−4.00 | >−4.00 |
| MCF7/ADR-RES | −5.95 | −8.48 | −4.80 | >−4.00 | >−4.00 | >−4.00 |
| MDA-MB-231/ATCC | −7.55 | −8.54 | −6.13 | −4.84 | −4.63 | −4.29 |
| MDA-MB-435 | <−8.00 | <−13.00 | <−8.00 | — | <−8.00 | — |
| MDA-N | <−8.00 | <−13.00 | <−8.00 | — | <−8.00 | — |
| SK-BR-3 | <−8.00 | — | −6.04 | — | >−4.00 | — |
| MDA-MB-468 | <−8.00 | — | −6.26 | — | >−4.00 | — |
| MAXF 401 | <−8.00 | — | <−8.00 | — | — | — |
| MG_MID | −7.79 | −10.15 | −5.59 | −4.54 | −4.32 | −4.06 |
| Delta | 0.21 | — | 2.41 | — | 3.68 | — |
| Range | 2.14 | 8.00 | 4.00 | 7.20 | 4.00 | 0.45 |

The 7-hexanoyltaxol compound of the present invention in most instances is as potent and in some instances more potent than paclitaxel. The data represented in Table I is graphically represented in FIGS. 2a and 2b through FIGS. 10a and 10b. Dose response curves, depicted in the above mentioned Figures, are obtained by exposing various cancer cell lines to compounds that have a known concentration ([log$_{10}$M]), as discussed in detail above, and then plotting the percentage growth of each cell line at each concentration. Percentage growth is determined by dividing the number or mass of cells in the test well by the number or mass of the cell in a control well. The following is an example of how the information in Table I and in the Figures is interpreted.

Figure 2A:
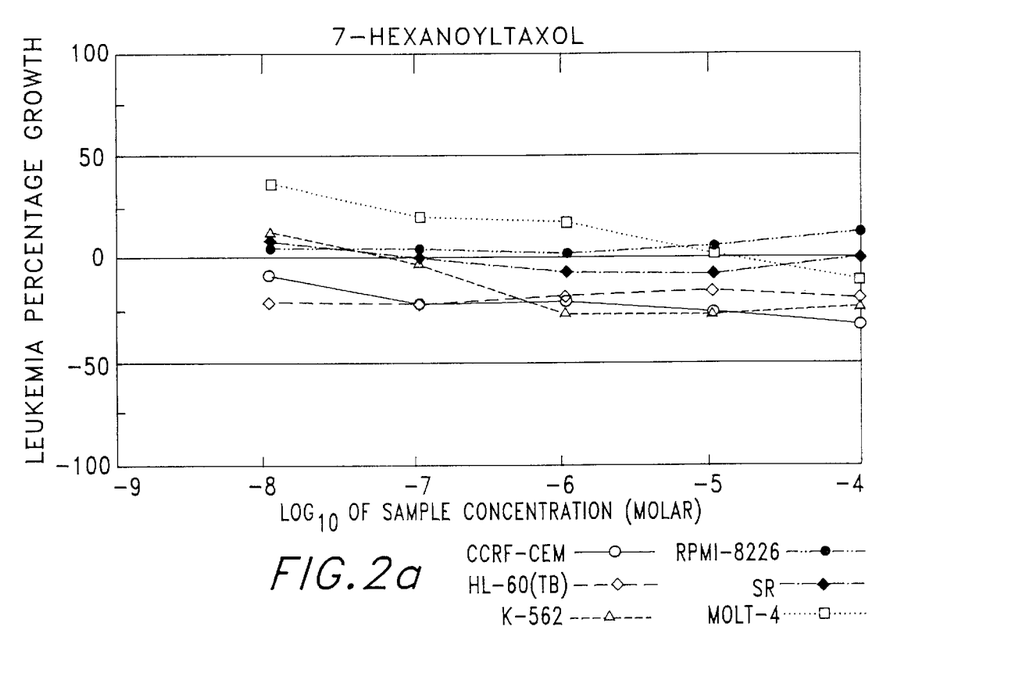
FIG. 2a depicts the dose response curves generated by exposing various leukemia cell lines to various concentrations of the composition of the present invention.
Figure 2B:
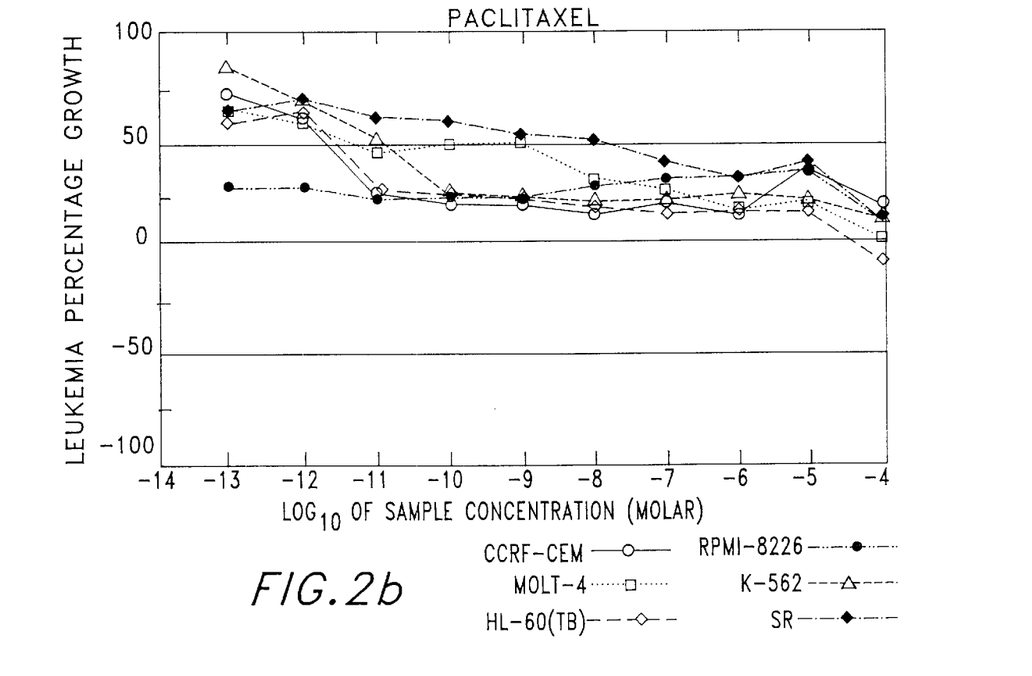
FIG. 2b depicts the dose response curves generated by exposing various leukemia cell lines to various concentrations of paclitaxel.
Figure 3A:
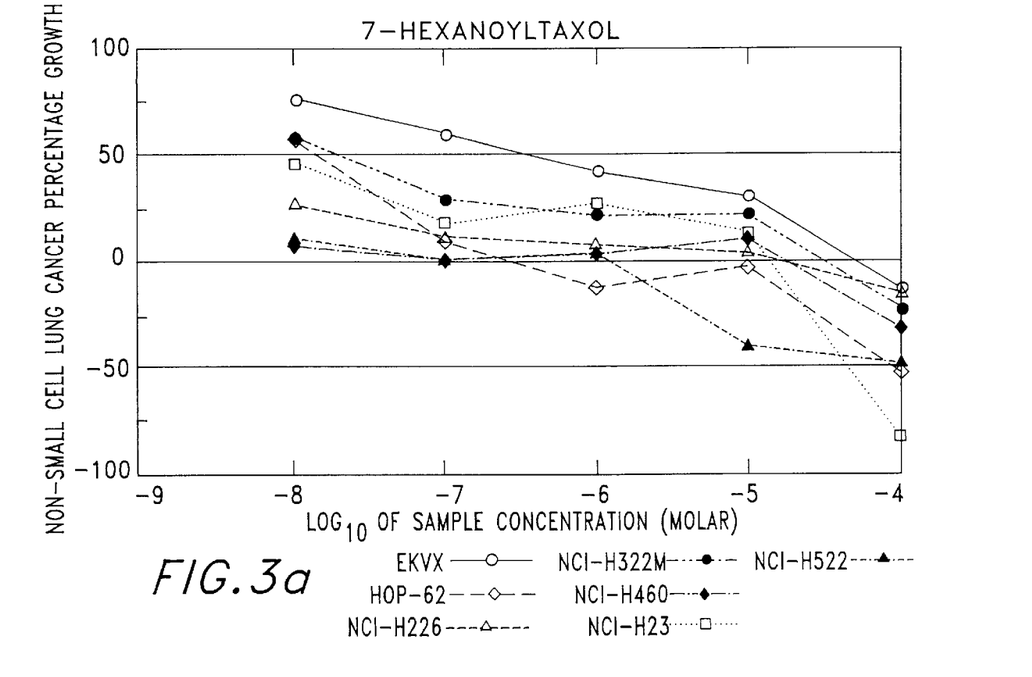
FIG. 3a depicts the dose response curves generated by exposing various non-small cell lung cancer cell lines to various concentrations of the composition of the present invention.
Figure 3B:
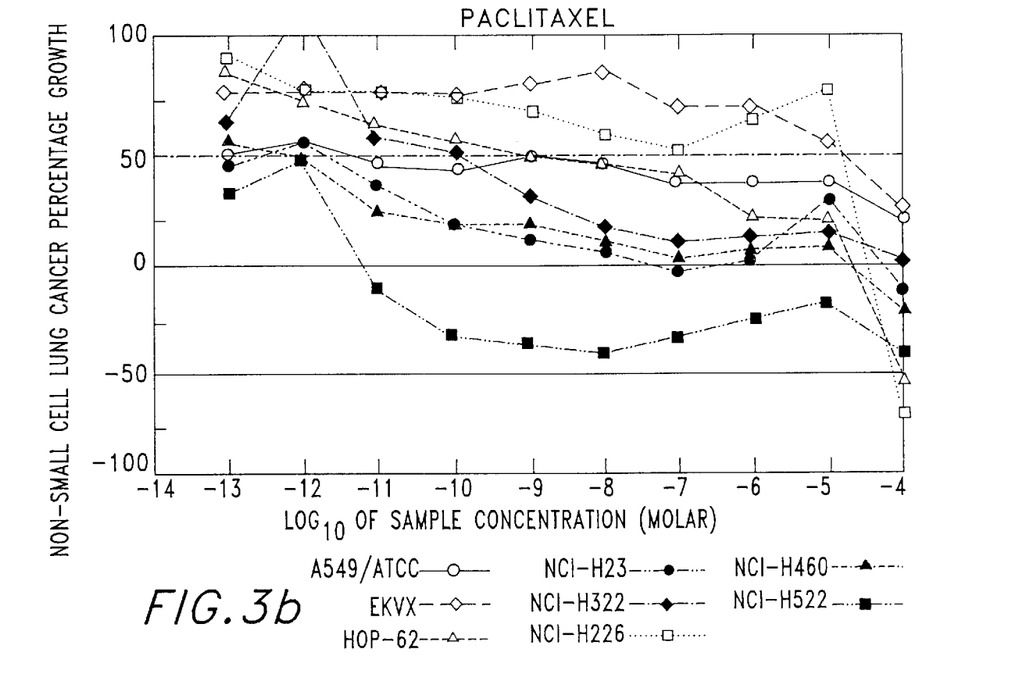
FIG. 3b depicts the dose response curves generated by exposing various non-small cell lung cancer cell lines to various concentrations of paclitaxel.
Figure 4A:
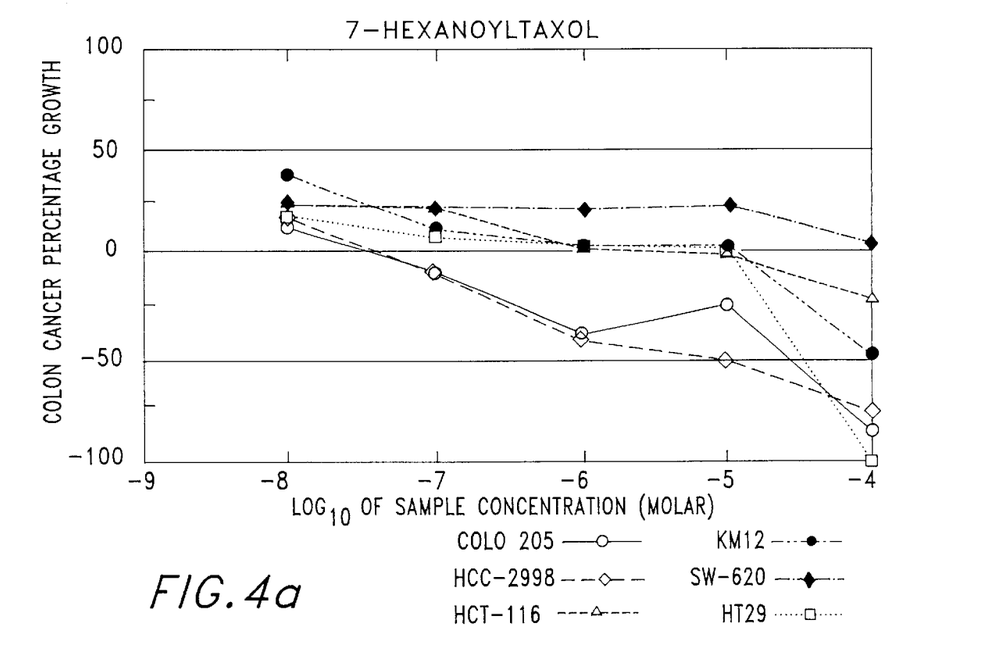
FIG. 4a depicts the dose response curves generated by exposing various colon cancer cell lines to various concentrations of the composition of the present invention.
Figure 4B:
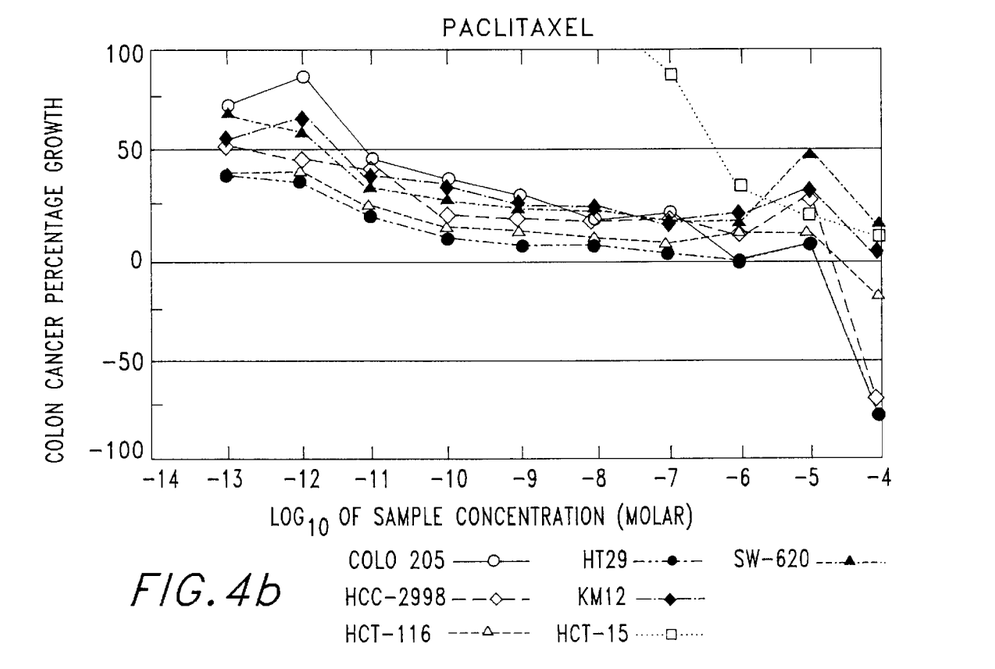
FIG. 4b depicts the dose response curves generated by exposing various colon cancer cell lines to various concentrations of paclitaxel.
Figure 5A:
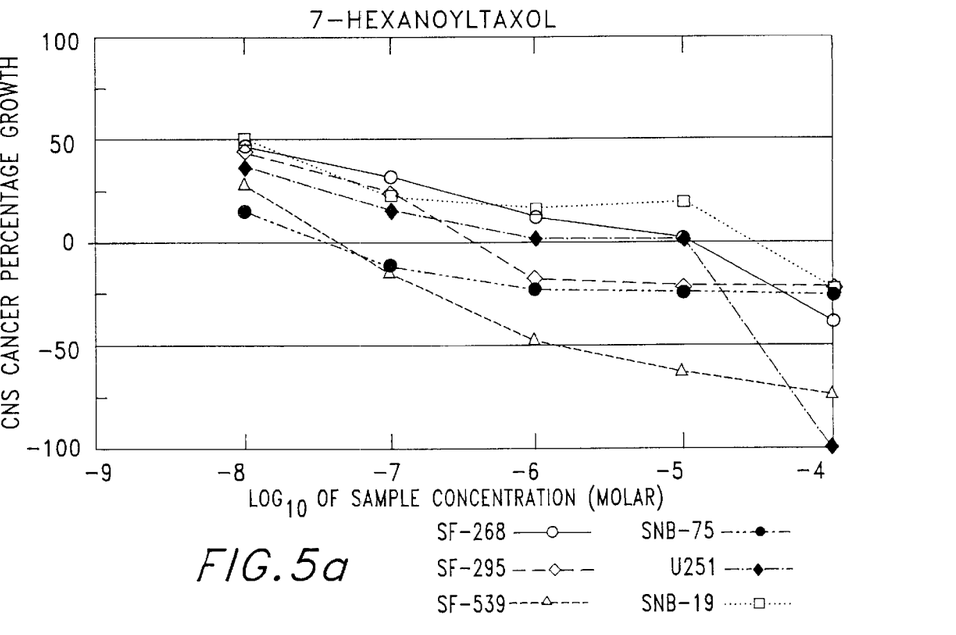
FIG. 5a depicts the dose response curves generated by exposing various CNS cancer cell lines to various concentrations of the composition of the present invention.
Figure 5B:
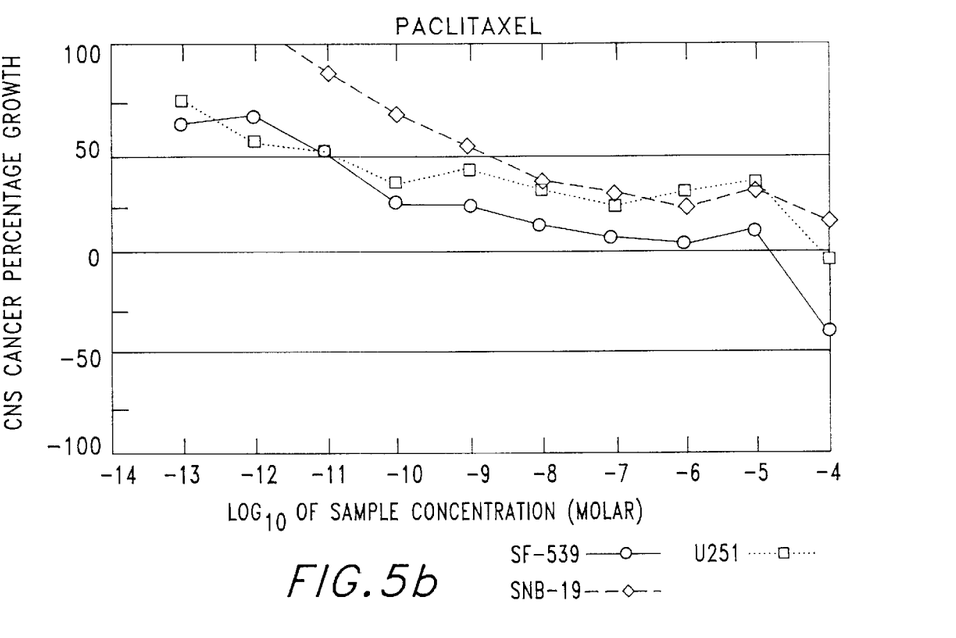
FIG. 5b depicts the dose response curves generated by exposing various CNS cancer cell lines to various concentrations of paclitaxel.
Figure 6A:
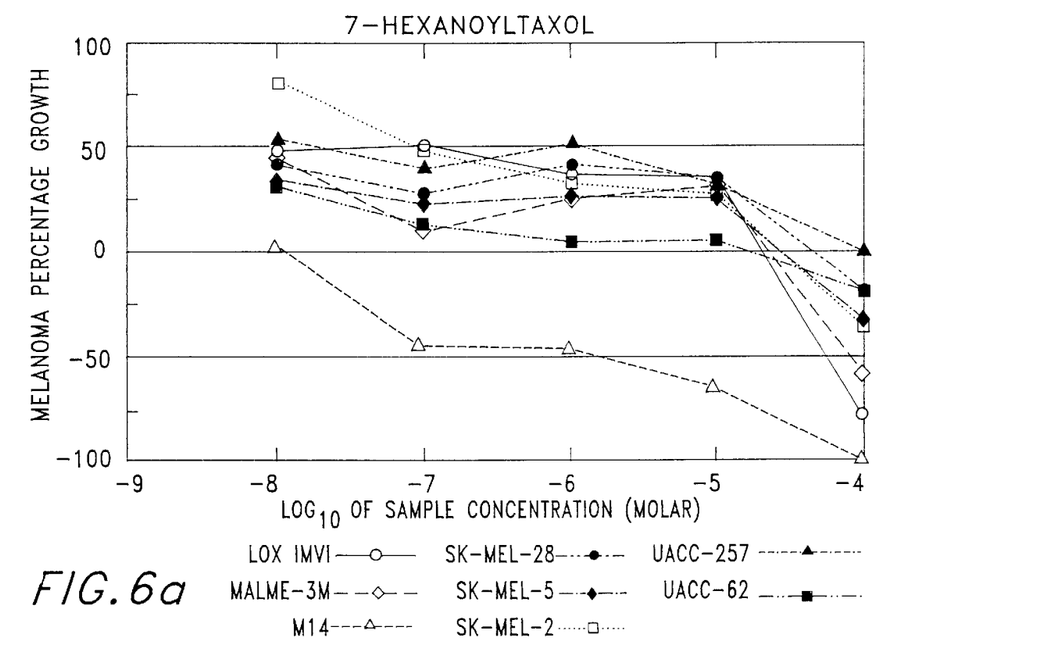
FIG. 6a depicts the dose response curves generated by exposing various melanoma cell lines to various concentrations of the composition of the present invention.
Figure 6B:
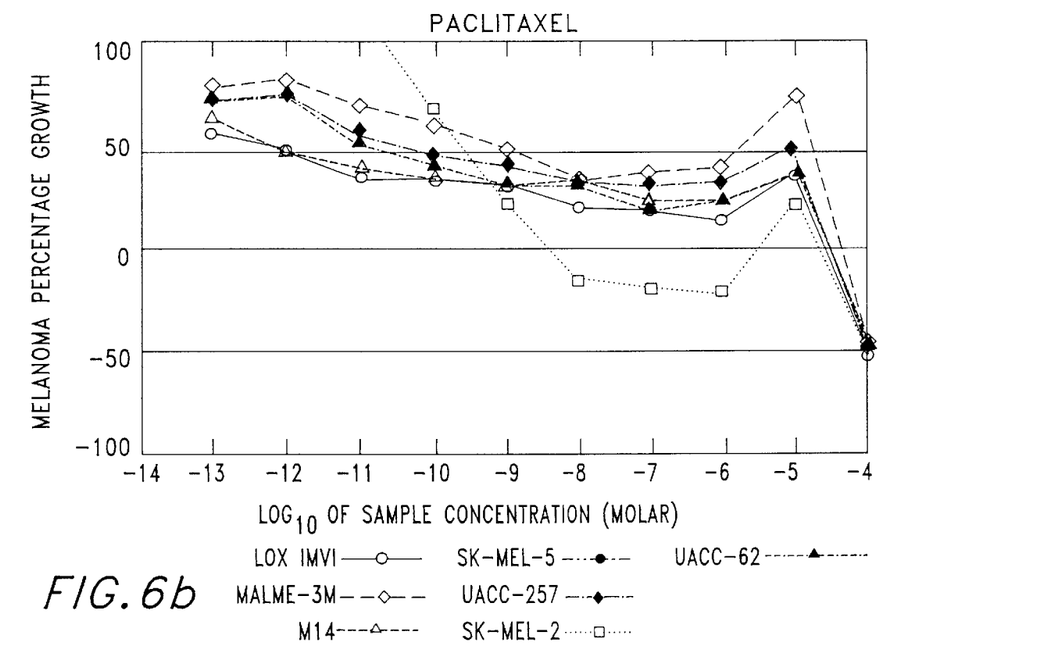
FIG. 6b depicts the dose response curves generated by exposing various melanoma cell lines to various concentrations of paclitaxel.
Figure 7A:
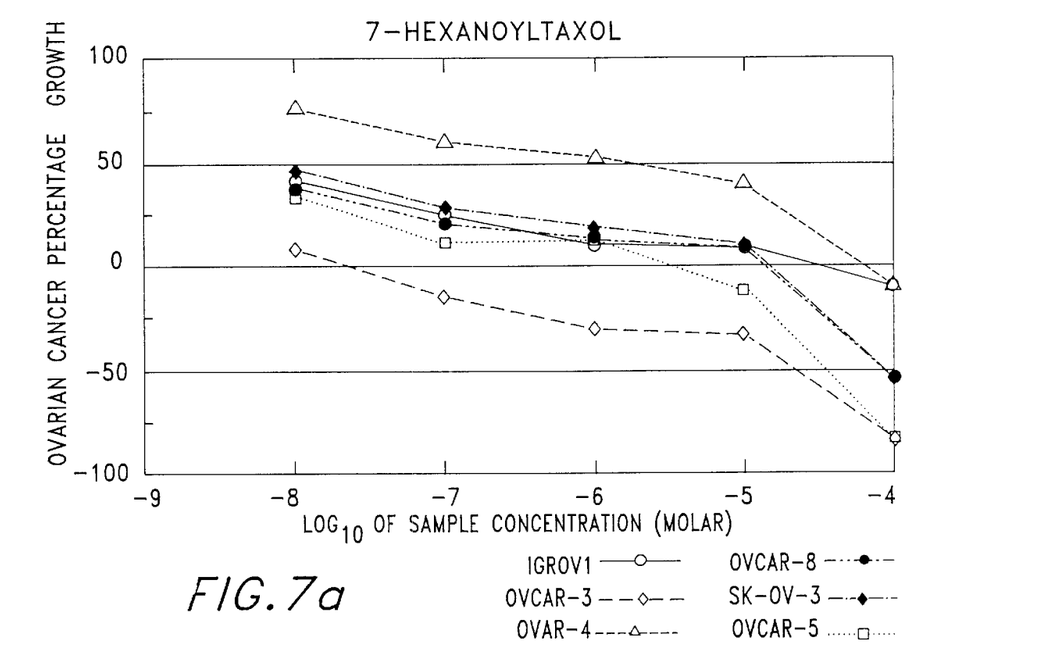
FIG. 7a depicts the dose response curves generated by exposing various ovarian cancer cell lines to various concentrations of the composition of the present invention.
Figure 7B:
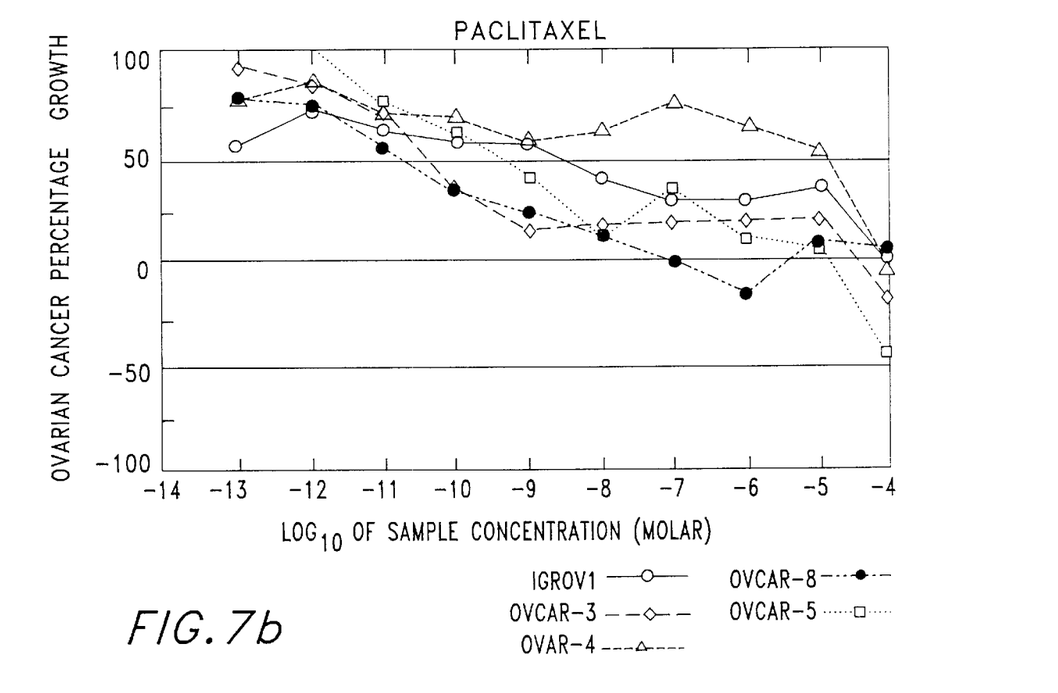
FIG. 7b depicts the dose response curves generated by exposing various ovarian cancer cell lines to various concentrations of paclitaxel.
Figure 8A:
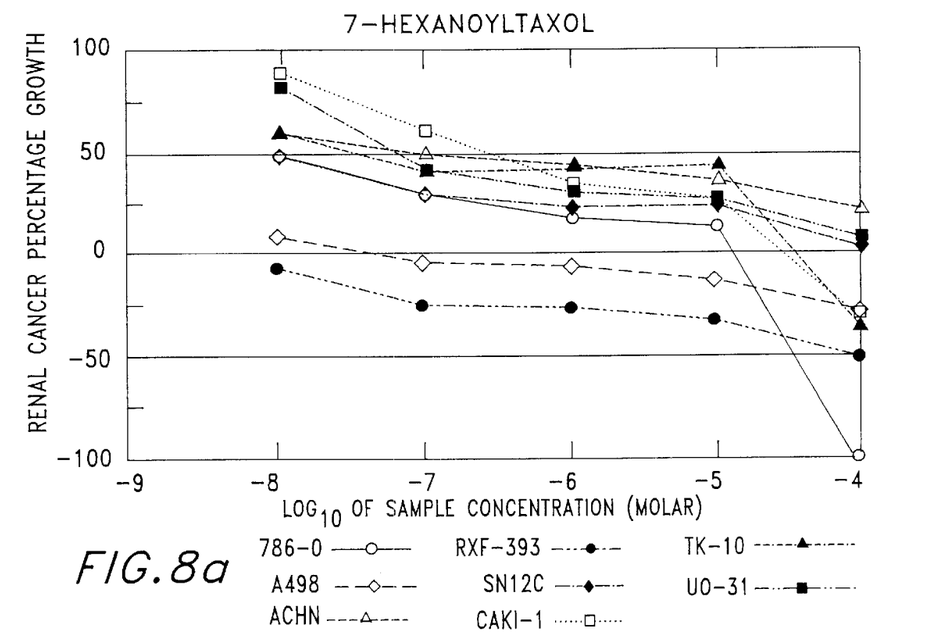
FIG. 8a depicts the dose response curves generated by exposing various renal cancer cell lines to various concentrations of the composition of the present invention.
Figure 8B:
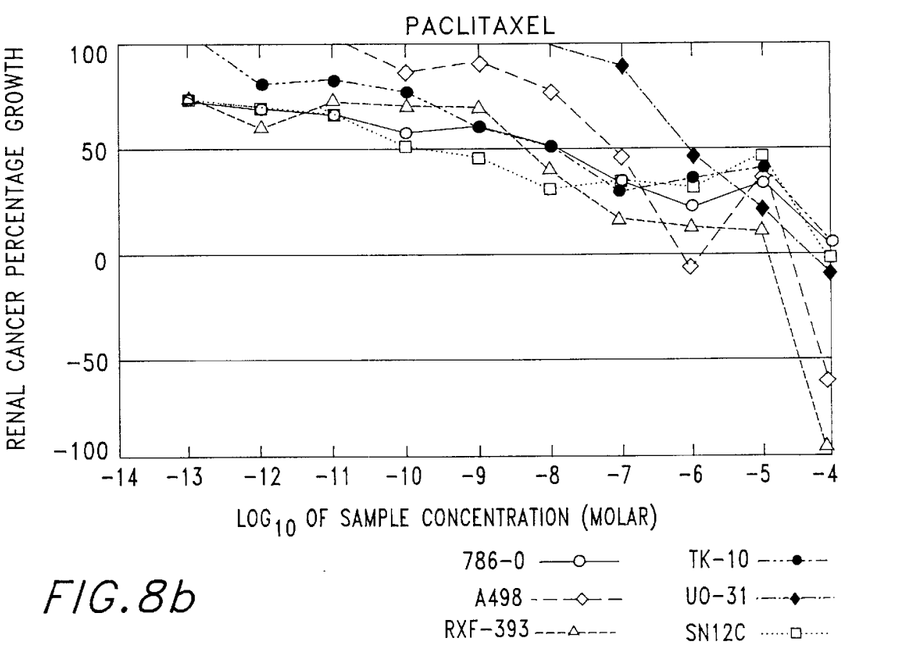
FIG. 8b depicts the dose response curves generated by exposing various renal cancer cell lines to various concentrations of paclitaxel.
Figure 9A:
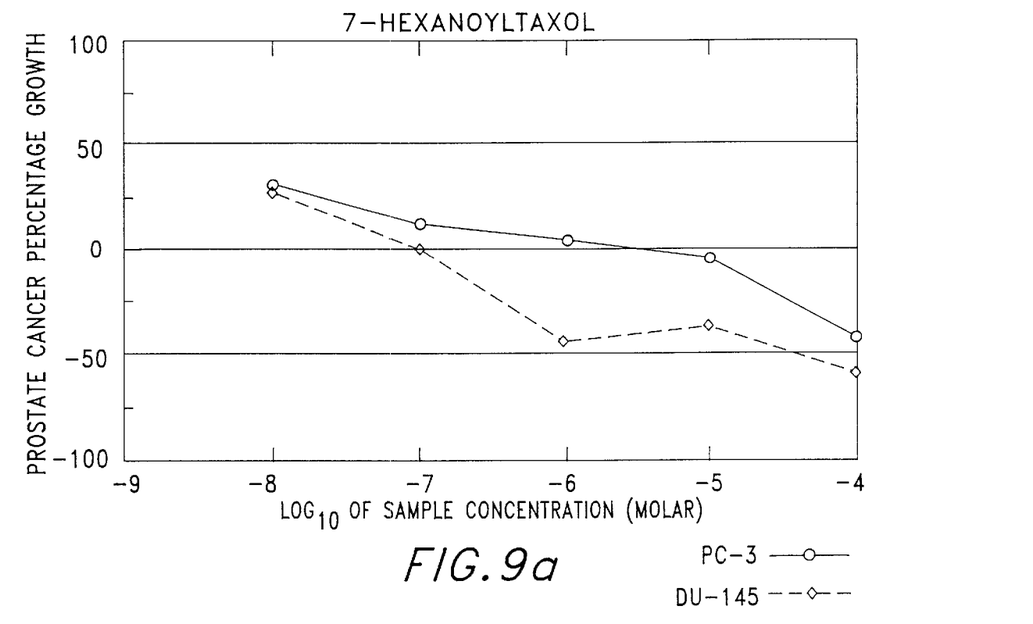
FIG. 9a depicts the dose response curves generated by exposing various prostate cancer cell lines to various concentrations of the composition of the present invention.
Figure 9B:
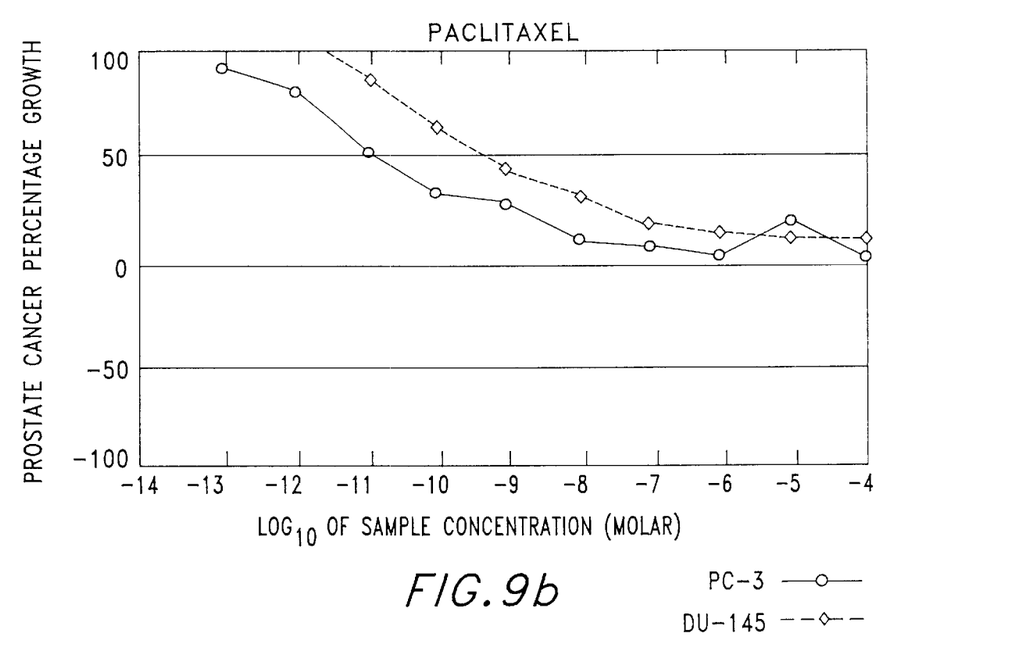
FIG. 9b depicts the dose response curves generated by exposing various prostate cancer cell lines to various concentrations of paclitaxel.
Figure 10A:
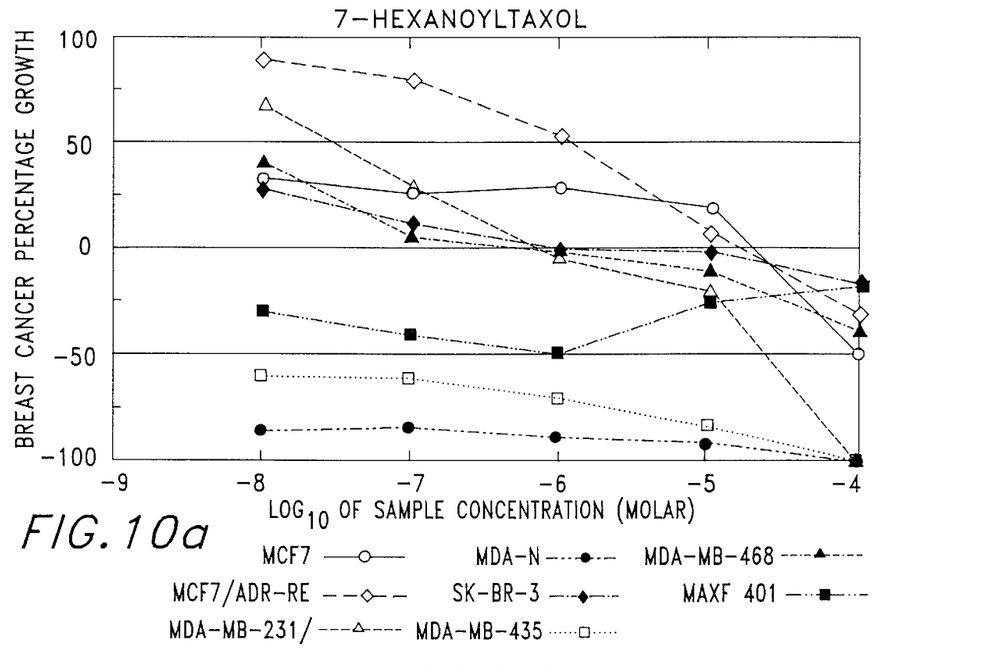
FIG. 10a depicts the dose response curves generated by exposing various breast cancer cell lines to various concentrations of the composition of the present invention.
Figure 10B:
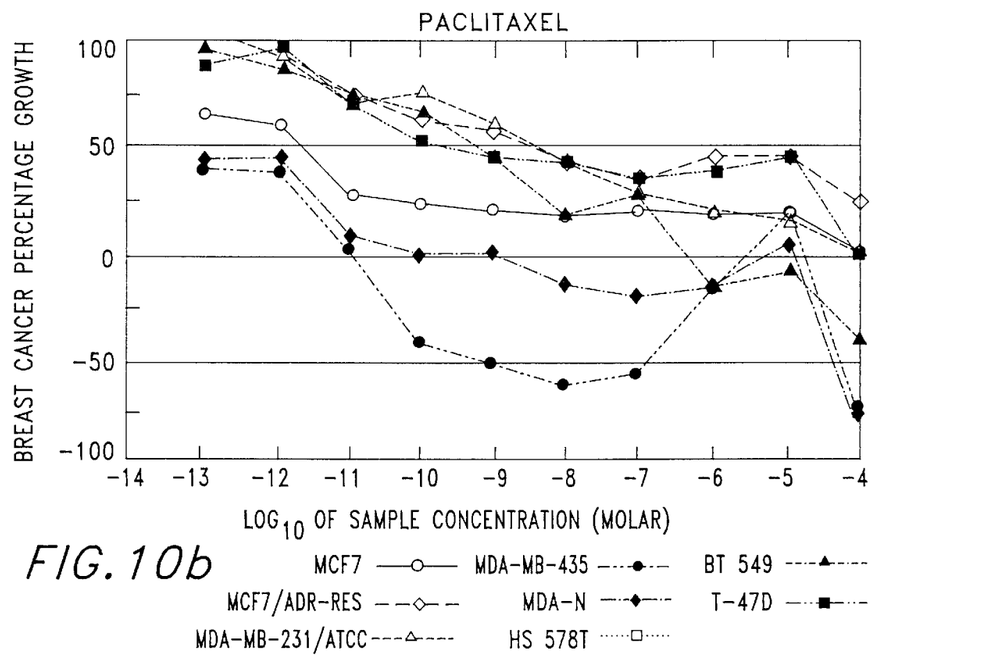
FIG. 10b depicts the dose response curves generated by exposing various breast cancer cell lines to various concentrations of paclitaxel.

Referring to the leukemia cell line CCRF-CEM, in FIGS. 2a and 2b the first comparison that is made between the compound of the present invention, 7-hexanoyltaxol, and paclitaxel are the concentrations of the two drugs which are necessary to inhibit growth, graphically represented as in FIGS. 2a and 2b as the concentration necessary to achieve the value of +50. As discussed previously, the five drug dilutions routinely tested range from 10$^{-4}$ to 10$^{-8}$ molar. Therefore, concentrations less than or greater than 10$^{-8}$ and 10$^{-4}$ molar, respectfully, that are required to achieve a desired result are not determined. Referring now to FIG. 2a, a concentration of approximately 10$^{-7}$ molar is necessary to achieve primary growth inhibition for the compound of the present invention. The lower concentrations for paclitaxel, however, have been determined for this drug and the concentration at which primary growth inhibition occurs using paclitaxel is −11.61 molar, see FIG. 2b. The concentration at which 7-hexanoyltaxol is considered cytostasis, i.e. percentage growth is equal to 0, is −6.1 molar, while an equivalent intensity using paclitaxel is achieved at a concentration greater than −4.00 molar. Cytotoxicity, i.e., the concentration for which the percentage growth is equal to −50, occurs for both drugs at some concentration greater than −4.00 molar.

The potency of the 7-hexanoyltaxol compound (5) of the present invention as compared to paclitaxel varies from cell line to cell line. However, on the whole, the potency of 7-hexanoyltaxol was found to be equivalent to and in many instances greater than that of paclitaxel's. The mean values for both 7-hexanoyltaxol and paclitaxel are listed at the end of the Table I. When interpreting these numbers, however, it is important to take into consideration that values above 10$^{-8}$ and below 10$^{-4}$ were not collected, this factor is reflected in the range.

The compound of the present invention was further tested on multidrug resistant cell lines. The resistance of cancer cells to multiple chemotherapeutic drugs which are structurally unrelated has been termed "multidrug resistance." In the past several years, several mechanisms of multidrug resistance have been described, including the expression of a cell surface multidrug efflux pump (P-glycoprotein or the multidrug transporter), altered glutathione metabolism, reduced activity of topoisomerase II, and various less clearly defined changes in cellular proteins. Because of evidence that expression of P-glycoprotein is associated with drug-resistance in cancer, P-glycoprotein has been studied extensively from the point of view of its biochemistry and mechanism of action in order to develop inhibitors which can be used clinically to reverse drug resistance of cancers in patients. The clinical significance of the other mechanisms of multidrug resistance are less well-established, but many model systems indicate that they may contribute to clinical resistance.

Surprisingly, compound of the present invention is effective in treating cancer cell lines that exhibit multidrug resistance. To determine the effect of 7-hexanoyltaxol (5) as compared to paclitaxel on multidrug resistant cell lines, screening assays were performed; the results are summarized in Table 2 below.

TABLE 2

| Compound | 26 Cell lines ($\mu$g/ml) | | | | | |
|---|---|---|---|---|---|---|
| | Mean IC50 | Min IC50 | MDR | rho | Tubulin ED50 | G2/M arrest MED($\mu$g/ml) |
| 7-hexanoyltaxol | 0.008 | 0.001 | 1 | 0.67 | 4.3 | 0.10 |
| Taxol | 0.020 | 0.001 | 158 | 1.00 | 2.1 | 0.025 |

KEY:
Mean IC50: 26 cell line Mean Growth inhibition IC50 value ($\mu$g/ml) .48 hour drug treatment, sulforhodamine stain.
Min IC50: Lowest observed IC50 value in 26 cell line screen.
MDR: The ratio of two IC50 values, where the numerator is an MDR$^+$ cell line. Higher numbers = less effective vs. MDR (multidrug resistant) cells.
rho: Mean Graph correlation coefficient, where 1 = identical pattern as Taxol; 0.85–0.95 = close match; 0.75–0.85 = good match; $\leq$0.75 = poor match.
Tubulin ED50: Concentration of taxane that causes 50% of purified calf-brain tubulin to to polymerize compared to the amximum polymerization produced by the the GRP control (1 mM).
G2/M arrest: Minimum concentration of taxane that results in 60% of CCRF-CEM cells to arrest in G2-M.

The 7-hexanoyltaxol compound (5) of the present invention is vastly more effective than paclitaxel against multidrug resistant cell lines.

The following non-limited example provides a specific high yield process for preparing 7-hexanoyltaxol. All scientific and technical terms have the meanings as understood by one with ordinary skill in the art. The synthetic descriptions and specific examples that follow are only intended for the purposes of illustration, and are not to be construed as limiting in any manner to make compounds of the present invention by other methods. The methods may be adapted to variation in order to produce compounds embraced by this invention but not specifically disclosed. Further, variations of the methods to produce the same compounds in somewhat different fashion will be evident to one skilled in the art.

All temperatures are understood to be in Centigrade (° C.) when not specified. The nuclear magnetic resonance (NMR) spectral characteristics refer to chemical shifts $\delta$ expressed in parts per million (ppm) versus tetramethylsilane (TMS) as reference standard. $^1$H and $^{13}$C NMR spectra were recorded on a Varian Gemini-400 instrument or JEOL Eclipse-400. The relative area reported for the various shifts in the proton NMR spectral data corresponds to the number of hydrogen atoms of a particular functional type in the molecule. The nature of the shifts as to multiplicity is reported as broad singlet (bs), broad doublet (bd), broad triplet (bt), broad quartet (bq), singlet (s), multiple (m), doublet (d), quartet (q), triplet (t), doublet of doublet (dd), doublet of triplet (dt), and doublet of quartet (dq). The solvents employed for taking NMR spectra are DMSO-d$_6$ (perdeuterodimethysulfoxide), D$_2$O deuterated water), CDCl$_3$ (deuterochloroform) and other conventional deuterated solvents. The chemical shifts are expressed in ppm relative to the reference of CDCl$_3$ or DMSO. Deuterated solvents were purchased from Aldrich Chemical Co. The infrared (IR) spectral description was measured on a KVB Analect Diamond-20 FT-IR Spectrometer featuring a Laser Precision XAD-Plus Microscope. Electrospray mass spectra were obtained from a VG Platform HPLC-MASS Spectrometer. TLC plates of silica gel 60F254 were purchased from E. M. Merck and kept in a closed container over Drierite® prior to use. Melting points were measured on a MEL-TEMP II apparatus equipped with a digital Barnant 100 Thermocouple Thermometer and are uncorrected. HPLC was performed on a Hitachi chromatographic spectrometer (L-6200A Intelligent Pump, D-6000 Interface, L-4000 UV Detector and AS-4000 Intelligent Auto Sampler). Combination of CH$_3$CN and H$_2$O in different concentrations are used as HPLC solvent system. All solvents were distilled before use. Commercially available chemicals were used without any further purification. Various methods of purifying the products of the present invention are known and understood by those skilled in the art and the purification methods presented in the Examples is solely listed by way of example and is not intended to limit the invention.

EXAMPLE I (I) Preparation of bis 2',7-Hexanoyltaxol:

Hexanoic anhydride 4.47 mL, 19.325 mmol) was added to a solution of paclitaxel (3.30 g, 3.865 mmol) and DMAP (0.047 g, 0.386 mmol) in 30 mL of CH$_2$Cl$_2$ at 0° C. The reaction mixture was stirred over a range of approximately 0–25° C. for 18 hours The reaction mixture was quenched with 5% NaHCO$_3$, and extracted with 3×25 mL of CH$_2$Cl$_2$. The combined organic layer was washed with water, and brine and dried with anhydrous MgSO$_4$. The crude product was purified in two batches by silica gel column chromatography (4×25 cm silica columns, 2.5 MeOH/CH$_2$Cl$_2$) to provide 4.24 g (104%) of pure bis-2',7-hexanoyltaxol and 0.6 g (15%) of product contaminated with a slower spot. This excess mass is due to the residual anhydride and acid impurities. Thus, the pure fraction was dissolved in 30 mL of CH$_2$Cl$_2$ and washed with 5% NaHCO$_3$ solution. The aqueous layer was extracted with 3×15 mL of CH$_2$Cl$_2$. The organic phase was dried with anhydrous MgSO$_4$ and concentrated in vacuo to provide 3.146 g (78%) of bis-2',7-hexanoyltaxol as a white solid: melting point 124–128° C.; $^1$H NMR (400 MHZ, CDCl$_3$) $\delta$ 0.84–0.90(m, 12H), 1.14(s, 3H), 1.18 (s, 3H), 1.23–1.33 (m, 16H), 1.53–1.68 (m, 8H), 1.56 (s, 3H), 1.78 (s, 3H), 1.79 (m, 1H), 1.98 (s,3H), 2.12–2.24 (m, 1H), 2.30–2.44 (m, 10H), 2.42 (s, 3H), 2.59 (m, 1H), 3.93 (d, J=7.0 Hz, 1H), 4.16 (d, J=8.4 Hz, 1H), 4.31 (d, J=8.4 Hz, 1H), 4.94 (dd, J=1.0, 8.0 Hz, 1H), 5.52 (d, 3.3 Hz, 1H), 5.57 (dd, J=7.0, 10.2 Hz, 1H), 5.66 (d, J=6.6 Hz, 1H), 5.92 (dd, J=3.7, 9.0 Hz, 1H), 6.20 (dd, J=8.8, 8.8 Hz, 1H), 6.26 (s, 1H), 6.88 (d, J=9.2 Hz, 1H), 7.32–7.42 (m, 7H), 7.48–7.52 (m, 3H), 7.59 (m, 1H), 7.73 (m, 2H), 8.10 (m, 2H)—some residual hexane solvent present; LRMS (electrospray) M/Z observed for C$_{59}$H$_{71}$NO$_{16}$Na (M+Na): 1072.9.

(II) Hydrolysis of the 2'-hexanoate group

NaHCO$_3$ (12.54 g, 149.8 mmol) was added to a mixture of bis-2',7-hexanoyltaxol (3.15 g, 3.0 mmol), H$_2$O$_2$ (30%, 10.08 mL), and THF (122 mL). The reaction mixture was stirred for 8 hours at room temperature and stored in a refrigerator overnight. Then the mixture was stirred for an additional 2 hours. Since the starting material has not yet been completely hydrolyzed about 100 mL of water was added and the mixture was stirred for an additional 6 hours. The reaction mixture was quenched with 5% citric acid carefully. The aqueous phase was extracted with 3×100 mL of CH$_2$Cl$_2$. The combined organic phase was washed with 20% Na$_2$S$_2$O$_3$ and brine, dried with anhydrous MgSO$_4$, and concentrated in vacuo to give a crude product. Repeated flash silica gel column chromatography (2% MeOH/CH$_2$Cl$_2$ for first column, 10–20% EtOAc/CH$_2$Cl$_2$ for second column) gave calculated 1 g (approximately 35%) of impure 7-hexanoyltaxol and 1.5 g (approximately 53%) of pure 7-hexanoyltaxol as a white solid: Melting Point 149–154° C.; $^1$H NMR (400 MHZ, CDCl$_3$) δ 0.86 (t, 7.0 Hz, 3H), 1.16 (m, 4H), 1.13 (m, 5H), 1.56 (m, 2H), 1.80 (s, 3H), 1.82 (m, 1H), 1.82 (s, 3H), 2.14 (s, 3H), 2.18–2.40 (m, 5H), 2.36 (s, 3H), 2.58 (m, 1H), 3.60 (d, J=4.8 Hz, 1H), 3.9 (d, J=6.6 Hz, 1H), 4.16 (d, J=8.4 Hz, 1H), 4.31 (d, J=8.4 Hz, 1H), 4.79 (d, J=1, 2.6 Hz, 1H), 4.92 (d, J=8.0 Hz, 1H), 5.53 (dd, J=7.3, 10.2 Hz, 1H), 5.65 (d, J=6.6 Hz, 1H), 5.80 (dd, J=2.2, 9.2 Hz, 1H), 6.15 (dd, J=8.8, 8.8 Hz, 1H), 6.22 (s, 1H), 7.10 (d, J=9.2 Hz, 1H), 7.35 (m, 1H), 7.41 (m, 4H), 7.48 (m, 5H), 7.60 (t, J=7 Hz, 1H), 7.74 (d, J=7.3 Hz, 2H), 8.09 (7.32 Hz, 2H); $^{13}$C NMR (125 MHZ, CD$_3$OD) δ 10.07, 12.91, 13.39, 19.31, 20.73, 21.85, 22.03, 23.78, 25.43, 30.98, 32.94, 33.65, 35.21, 43.30, 47.24, 55.93, 56.36, 56.45, 70.85, 71.47, 73.50, 74.55, 75.24, 75.98, 77.55, 80.64, 83.84, 127.16, 127.17, 127.67, 128.26, 128.39, 128.41, 129.86, 129.98, 131.52, 133.13, 133.29, 134.31, 138.67, 140.71, 166.26, 169.07, 169.28, 170.64, 173.13, 202.30. LRMS (electrospray) M/Z observed for C$_{53}$H$_{61}$NO$_{15}$ (M+H): 952.8, and M/Z observed for C$_{53}$H$_{61}$NO$_{15}$Na (m+Na): 974.8.

The embodiments of the invention in which an exclusive property or privilege is claimed are defined as follows:

1. A method for treating multi-drug resistant cancer in a human suffering from multi-drug resistant cancer comprising: administering to a human a taxane derivative of formula:

2. The method of claim 1, wherein the multi-drug resistant cancer is selected from the group consisting of leukemia, non-small cell lung cancer, color cancer, CNS cancer, melanoma, ovarian cancer, renal cancer, prostate cancer, and breast cancer.

3. A method of treating multi-drug resistant cells in a human comprising: administering to a human having multi-drug resistant cells a compound having the formula wherein R is a monovalent organic compound, a monovalent aliphatic compound, a monovalent cyclic group, or a branched or unbranched alkyl, alkenyl, alkynyl group or aryl group.

4. The method of claim 3, wherein the cells proliferate in an uncontrolled manner.

5. The method of claim 4, wherein the cells are cancer cells.

6. The method of claim 5, wherein the cancer is selected from the group consisting of leukemia, non-small cell lung cancer, color cancer, CNS cancer, melanoma, ovarian cancer, renal cancer, prostate cancer, and breast cancer.

7. The method of claim 3, wherein said monovalent aliphatic compound is a hydrocarbon or a hetero-acyclic group.

8. The method of claim 3, wherein said monovalent cyclic group is an alicyclic or aromatic group.

9. The method of claim 8, wherein said monovalent alicyclic group comprises monovalent carbocyclic and heterocyclic groups.

10. The method of claim 8, wherein said monovalent aromatic group comprises monovalent carboaromatic groups and monovalent hetero-aromatic groups.

11. The method of claim 3, wherein the compound has the following formula

12. A method of ameliorating the symptoms of a cancer that is resistant to at least one chemotherapeutic agent in a human suffering from the cancer comprising: administering to a human suffering from the cancer a compound having the formula:

wherein R is a monovalent organic compound, a monovalent aliphatic compound, a monovalent cyclic group, or a branched or unbranched alkyl, alkenyl, alkynyl group or aryl group.

13. The method of claim 12, wherein the cancer is multi-drug resistant.

14. The method of claim 12, wherein said monovalent aliphatic compound is a hydrocarbon or a hetero-acyclic group.

15. The method of claim 12, wherein said monovalent cyclic group is an alicyclic or aromatic group.

16. The method of claim 15, wherein said monovalent alicyclic group comprises monovalent carbocyclic and heterocyclic groups.

17. The method of claim 15, wherein said monovalent aromatic group comprises monovalent carboaromatic groups and monovalent hetero-aromatic groups.

18. The method of claim 12, wherein the compound has the following formula

19. The method of claim 12, wherein the cancer is selected from the group consisting of leukemia, non-small cell lung cancer, color cancer, CNS cancer, melanoma, ovarian cancer, renal cancer, prostate cancer, and breast cancer.

* * * * *